United States Patent
Chen et al.

(10) Patent No.: US 11,220,478 B2
(45) Date of Patent: Jan. 11, 2022

(54) PREPARATION METHOD FOR 4-PHENYLTHIO-BENZENETHIOL

(71) Applicants: Zhejiang NHU Company Ltd., Shaoxing (CN); Zhejiang University, Hangzhou (CN); Zhejiang NHU Special Materials Co., Ltd., Shaoxing (CN)

(72) Inventors: Zhirong Chen, Hangzhou (CN); Woyuan Li, Shaoxing (CN); Hong Yin, Hangzhou (CN); Guiyang Zhou, Shaoxing (CN); Haoran Li, Hangzhou (CN); Shuaifeng Pan, Shaoxing (CN); Ming Lian, Shaoxing (CN); Guangde Qin, Shaoxing (CN); Qichuan Li, Shaoxing (CN)

(73) Assignees: Zhejiang NHU Company Ltd., Zhejiang (CN); Zhejiang University, Zhejiang (CN); Zhejiang NHU Special Materials Co., Ltd., Zhejiang (CN)

( * ) Notice: Subject to any disclaimer, the term of this patent is extended or adjusted under 35 U.S.C. 154(b) by 0 days.

(21) Appl. No.: 16/955,511

(22) PCT Filed: Jul. 12, 2018

(86) PCT No.: PCT/CN2018/095380
§ 371 (c)(1),
(2) Date: Jun. 18, 2020

(87) PCT Pub. No.: WO2019/119785
PCT Pub. Date: Jun. 27, 2019

(65) Prior Publication Data
US 2021/0009514 A1    Jan. 14, 2021

(30) Foreign Application Priority Data

Dec. 22, 2017 (CN) .......................... 201711408777.1

(51) Int. Cl.
*C07C 319/20* (2006.01)
*C01D 5/02* (2006.01)

(52) U.S. Cl.
CPC .............. *C07C 319/20* (2013.01); *C01D 5/02* (2013.01)

(58) Field of Classification Search
CPC ................................ C07C 319/20; C01D 5/02
See application file for complete search history.

(56) References Cited

U.S. PATENT DOCUMENTS 5,338,886 A    8/1994 Rule et al.
9,587,074 B2    3/2017 Chiong et al.

FOREIGN PATENT DOCUMENTS

| CN | 1590371 | * | 3/2005 | ............... C01D 5/02 |
|----|---------|---|--------|---------|
| CN | 1590371 A | | 3/2005 | |
| CN | 106633062 A | | 5/2017 | |
| CN | 108129368 A | | 6/2018 | |
| JP | 01106858 A | | 4/1989 | |
| JP | 04182463 A | | 6/1992 | |
| JP | 0578308 A | | 3/1993 | |
| JP | 2016532770 A | | 10/2016 | |
| WO | 2016133739 A1 | | 8/2016 | |

OTHER PUBLICATIONS

Bravo et al. ("Oxidation of Organic Sulfides by Br2 and H2O2. Electrophilic and Free-Radical Processes", J. Org. Chem., Apr. 2001, vol. 66, Issue 9, pp. 3232-3234) (Year: 2001).*
Chen et al., "A High-Efficiency Hybrid White Organic Light-Emitting Diode Enabled by a New Blue Fluorophor", J. Mater. Chem. C., 3:4283-89 (2015).
Mao et al., Improvement on the Synthesis of 1,2-Benzenedithiol, Fine Chemical Intermediates, 40(6):43, 44, 55 (2010) (w/ English abstract).
Pinchart et al., "Functionalized p-Phenylene Sulfides Synthesis of New Molecular Wires", Tetrahedron Letters, 39:543-46 (1998).
State Intellectual Property Office of the P.R. China, International Search Report and Written Opinion for International Application No. PCT/CN2018/095380, dated Sep. 12, 2018, 9 pages.

* cited by examiner

*Primary Examiner* — Rosalynd A Keys
(74) *Attorney, Agent, or Firm* — RatnerPrestia

(57) ABSTRACT

The present disclosure discloses a preparation method for 4-phenylthio-benzenethiol. The preparation method comprises the following steps: subjecting phenyl sulfide as a raw material to a halogenation reaction to obtain 4-halophenyl sulfide; subjecting the 4-halophenyl sulfide to a sulfhydrylation reaction to obtain a 4-phenylthio-phenylthiolate; and subjecting the 4-phenylthio-phenylthiolate to acidification. The preparation method of the present disclosure avoids the use of materials such as thiophenol which pollutes the environment, and realizes efficient recycling of the reaction materials, solvents, water and the like. The preparation method of the present disclosure is a green process for the synthesis of 4-phenylthio-phenylthiol without organic waste, waste acid and waste water discharge.

19 Claims, No Drawings

PREPARATION METHOD FOR 4-PHENYLTHIO-BENZENETHIOL

CROSS-REFERENCE TO RELATED APPLICATIONS

This application is a U.S. national phase application of International Application No. PCT/CN2018/095380, filed Jul. 12, 2018, which claims priority to Chinese Application No. 201711408777.1 filed Dec. 22, 2017, the contents of each of which are incorporated herein by their entireties for all purposes.

TECHNICAL FIELD

The present disclosure relates to a preparation method for 4-phenylthio-benzenethiol, and belongs to the field of organic chemical synthesis.

BACKGROUND

As publics have become more aware of environmental concerns, regulations governed in halogen in all countries are become more stringent, and among them, Europe stipulates that the content of bromine and the content of chloride contained in materials used in the electronics industry are less than 900 ppm, respectively. Nowadays, 70% of polyphenylene sulfide (hereinafter referred to as PPS) products are applied to the electronics and electrical industries as well as the automobile industry. However, due to limitations of the sodium sulfide method, PPS contains a large number of chloride terminal groups, which causes conventional PPS resin is products are barely up to the requirements for current regulations governed in halogen.

Cited Literature 1 discloses a method for preparing PPS having low chloride content by using p-thiophenoxy thiophenol (hereinafter referred to as PTT) as a blocking agent; as compared to known blocking agents, the PTT has the following significant advantages: because of an addition of a substituent —S—C$_6$H$_5$ to the para-position, the activity at the para-position increases, such that the PTT has a superior effect of reducing the chloride content in PPS to currently reported blocking agents; and after blocking, the structure of the terminal group of the polymer is similar to that of the molecular chain of the PPS, so the blocking has little to no effect on properties of the PPS resin.

Nonetheless, there are few studies on methods for synthesis of PTT in the prior art.

Cited Literature 2 publishes a method of synthesis of PTT as a blocking agent, and its synthesis route is described below (a process of synthesis of 4-phenylthio-benzenethiol). In this method, thioanisole as a starting material reacts with liquid bromine in acetic acid at 100° C. to generate 4-bromothioanisole, and then reacts with thiophenol in a mixed solvent of quinoline and pyridine at 160° C. in the presence of Cu$_2$O as a catalyst to produce 1-methylthio-4-(benylthio)benzene, to which 5% parts by mass of sodium 1-propanethiolate is added with DMF as a solvent, and reacts for 2 to 3 hours at 160° C. to give 4-phenylthio-benzenethiol having a yield of 93%.

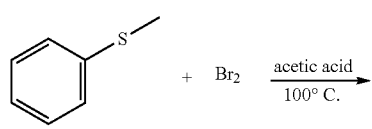

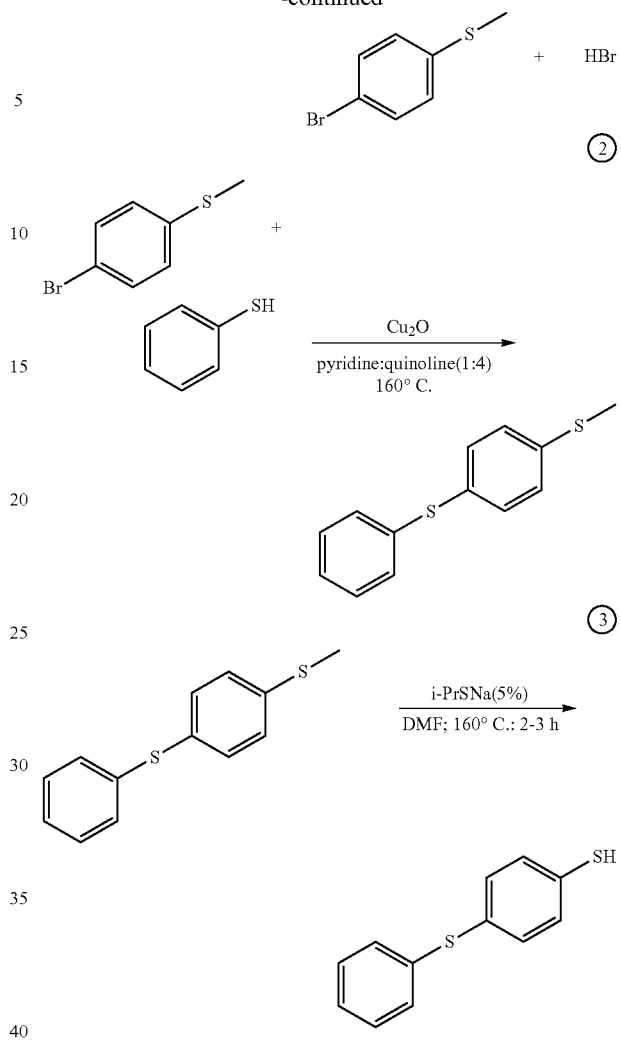

In this method, the preparation process is complicated, solvents are different in each step, while atom utilization of bromine is low, and thiophenol is used as a raw material in step ②, which easily leads to environmental issues in the preparation process.

In Cited Literature 3, the method for introducing a phenyl mercapto group is shown below (the reaction mechanism of converting hydroxyl to sulfhydryl). This method is costly due to use of an expensive fluorine-containing compound and a ligand palladium catalyst.

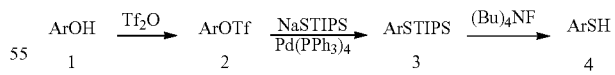

In Cited Literature 4, a halogenated aromatic compound used as a raw material reacts with thiourea in the presence of a nickel-based catalyst to prepare corresponding aromatic thiol. This method not only results in a great consumption of catalyst, but also a low yield of only 55% approx.

In Cited Literature 5, disulfide is used to prepare a thiol compound. This method uses Mg as a catalyst and a methanol as a solvent, so the yield is very high. However, this method can only be suitable for simple aromatic thiol compounds, but it is not applicable to PTT.

In conclusion, although synthesis methods for PTT have been reported, the improvements over cost control, yield, environmental friendliness and other aspects are not sufficient, and it is difficult to meet higher requirements for large scale production in industry.

LIST OF CITED LITERATURES

Cited Literature 1: CN201611260486.8
Cited Literature 2: Tetrahedron Letters, 1998, Vol. 39, No. 7, p. 543-546
Cited Literature 3: Tetrahedron Letters, 1996, Vol. 37, No. 26, p. 4523-4524
Cited Literature 4: U.S. Pat. No. 5,338,886
Cited Literature 5: Synthetic Communications, 1997, Vol. 27, Issue 8

SUMMARY

Technical Problem

In view of problems existing in the above prior art literatures, the present disclosure provides a preparation method for 4-phenylthio-benzenethiol. The preparation method for 4-phenylthio-benzenethiol introduces a new synthetic route avoiding use of matters, such as thiophenol, that pollutes the environment, and realizes highly efficient recycling of reaction mass, solvents, water and the like. The preparation method is environmentally friendly and thus is a green technique of synthesizing 4-phenylthio-benzenethiol.

Solution to Problem

The present disclosure provides a preparation method for 4-phenylthio-benzenethiol, comprising the steps of:

subjecting phenyl sulfide as a raw material to a halogenation reaction to obtain 4-halophenyl sulfide;

subjecting the 4-halophenyl sulfide to a sulfhydrylation reaction to obtain 4-phenylthio-phenylthiolate; and subjecting the 4-phenylthio-phenylthiolate to acidification.

According to the preparation method described above, the halogenation reaction is: adding peroxide to a mixed solution containing phenyl sulfide, an organic solvent, a halogenating agent, and an inorganic acid to undergo a halogenation reaction, and obtaining 4-halophenyl sulfide by separation;

the sulfhydrylation reaction is: subjecting the resulting 4-halophenyl sulfide and a SMAB-NaHS complex to a sulfhydrylation reaction, and obtaining an aqueous layer containing 4-phenylthio-phenylthiolate by extraction and separation; and the acidification reaction is: subjecting the aqueous layer containing 4-phenylthio-phenylthiolate to an acidification reaction in an acidic aqueous solution, and obtaining the 4-phenylthio-benzenethiol by separation.

According to the preparation method described above, in the halogenation reaction, the halogenating agent is one or more selected from the group consisting of sodium halides and potassium halides, preferably sodium halides; the inorganic acid is one or more selected from the group consisting of sulfuric acid, hydrochloric acid, and phosphoric acid, preferably sulfuric acid; based on 1 mol of phenyl sulfide, an amount of the halogenating agent is from 0.9 to 1.0 mol, preferably from 0.95 to 0.99 mol; and an amount of the inorganic acid is from 0.9 to 1.0 mol, preferably from 0.95 to 0.99 mol.

According to the preparation method described above, in the halogenation reaction, the organic solvent is one or more selected from the group consisting of dichloromethane, chloroform, carbon tetrachloride, and dichloroethane, preferably dichloromethane, or in some instances, the above reagents can also be dominated together with a small amount (for example, not more than 10% by mass of the solvent) of other solvents such as NMP and water; based on 1 mol of phenyl sulfide, an amount of the organic solvent is from 4 to 6 mol.

According to the preparation method described above, in the halogenation reaction, the peroxide is hydrogen peroxide; an amount of the peroxide is from 0.45 to 0.5 mol based on 1 mol of phenyl sulfide; the time of adding the peroxide is controlled at 2 to 10 hours, and the peroxide is preferably added dropwise.

According to the preparation method described above, in the halogenation reaction, the temperature for the halogenation reaction is from 10° C. to 40° C., and a total reaction time is from 4 to 15 hours.

According to the preparation method described above, in the sulfhydrylation reaction, based on 1 mol of phenyl sulfide, an amount of the SMAB-NaHS complex is from 0.9 to 1.0 mol, preferably from 0.95 to 0.99 mol.

According to the preparation method described above, in the sulfhydrylation reaction, the SMAB-NaHS complex is prepared by the following method:

a. adding a sodium hydroxide aqueous solution to an NMP solvent, and after the reaction is completed, subjecting the reactant to dehydration; and b. adding a sodium hydrosulfide aqueous solution prior to dehydration to obtain a SMAB-NaHS complex.

According to the method for preparing the SMAB-NaHS complex, based on 1 mol of phenyl sulfide, an amount of the sodium hydroxide is from 0.9 to 1.0 mol; an amount of the NMP solvent is from 4.0 to 5.0 mol; and an amount of the sodium hydrosulfide is from 0.9 to 1.0 mol.

According to the method for preparing the SMAB-NaHS complex, the dehydration in steps a and b is carried out at 180° C. to 250° C.

According to the preparation method described above, the sulfhydrylation reaction is carried out at 150° C. to 230° C., preferably 180° C. to 210° C.; the time of the sulfhydrylation reaction is 3 to 6 hours.

According to the preparation method described above, after the sulfhydrylation reaction is completed, desolvation is performed prior to extraction and separation. A solvent, such as NMP, recycled by desolvation can be directly used for the preparation of a SMAB-NaHS complex.

According to the preparation method described above, after the halogenation reaction is completed, an aqueous layer and an organic layer are obtained by separation, where the aqueous layer is used as an acidic aqueous solution in the acidification reaction; and the organic layer is desolventized and recycled to obtain a solvent, to which water is added, for use in extraction carried out following the sulfhydrylation reaction. An organic layer obtained by extraction and separation after the sulfhydrylation reaction is used as a solvent in the halogenation reaction.

According to the preparation method described above, delamination is performed following the acidification reaction; the resulting aqueous layer is subjected to cooling crystallization to give $Na_2SO_4$ containing crystal water; and the remaining mother solution is concentrated and then used as a raw material for the halogenation reaction.

Beneficial Effects

The preparation method for 4-phenylthio-benzenethiol as provided herein has the following excellent effects:

(1) the present disclosure selects low-odor phenyl sulfide in stead of conventional stink thiophenol, which contributes to amelioration of production environment; and phenyl sulfide derives from a wealth of sources and the cost of PTT synthesis can be greatly reduced;

(2) the preparation method for PTT as provided herein is very simple and can realize recycling of a halogenating agent, an organic solvent and water, while keeping the halogen atom always in the reaction system, and the acids and alkalis used in the reactions are all controlled within the reaction amounts without extra acidic and alkaline waste water; the recycling of the resulting products is up to 100% and no organic wastes are discharged, which is a green technique of synthesizing 4-phenylthio-benzenethiol;

(3) the by-product $Na_2SO_4 \cdot 10H_2O$ produced herein has a high purity and can be directly used as an individual product, which increases the economical efficiency of the present disclosure.

DETAILED DESCRIPTION

Here are detailed illustrations of the modes of implementing the present disclosure.

The First Embodiment

In the first embodiment, the present disclosure provides a preparation method for 4-phenylthio-benzenethiol, comprising the steps of: subjecting phenyl sulfide as a raw material to a halogenation reaction to obtain halophenyl sulfide, in an embodiment of the present disclosure, the halophenyl sulfide being 4-halophenyl sulfide; subjecting the 4-halophenyl sulfide and a sulfhydrylization agent to a sulfhydrylation reaction to obtain 4-phenylthio-phenylthiolate; and subjecting the 4-phenylthio-phenylthiolate to acidification to obtain 4-phenylthio-benzenethiol.

Specifically, the preparation method comprises the following steps:

1) a halogenation reaction: a peroxide is added to a mixed solution including phenyl sulfide, an organic solvent, a halogenating agent, and an inorganic acid to undergo a bromination reaction, and upon completion of reaction, delamination is performed, and the organic solvent is removed from an organic layer to obtain 4-halophenyl sulfide;

2) a sulfhydrylation reaction: the 4-halophenyl sulfide obtained in step 1) and a SMAB-NaHS complex are subjected to a sulfhydrylation reaction, and after the reaction is completed, extraction and delamination are carried out to obtain an aqueous layer containing 4-phenylthio-phenylthiolate; the SMAB is a sodium 4-methylamino-butyrate, and the NaHS is sodium hydrosulfide; and 3) an acidification reaction: the aqueous layer containing 4-phenylthio-phenylthiolate is subjected to an acidification reaction in an acidic aqueous solution, and after the reaction is completed, delamination is carried out and the organic layer is 4-phenylthio-benzenethiol.

Halogenation Reaction

In the present embodiment, phenyl sulfide used as a raw material is subjected to a halogenation reaction to obtain 4-halophenyl sulfide. The phenyl sulfide has an advantage of low odor, which is beneficial to amelioration of the production environment; besides, the phenyl sulfide derives from a wealth of sources, which can greatly reduce the cost of PTT synthesis.

In the present embodiment, the mode or condition of carrying out the halogenation reaction is not in particular limited, for example, in the halogenation reaction, a halogenating agent is used together with phenyl sulfide for the halogenation reaction, and conventional temperature and pressure in the art are provided. In the meantime, inorganic acids, typically sulfuric acid, or the like may alternatively be used as a component of an additive.

In step 1), peroxide is slowly added, preferably added dropwise, to a mixed solution containing phenyl sulfide, an organic solvent, a halogenating agent, and an inorganic acid to undergo a halogenation reaction. The speed of the halogenation reaction can be efficiently controlled by controlling the time of adding the peroxide. The peroxide, not particularly limited, may be peroxide generally used in this field, and typically, hydrogen peroxide or the like may be usable. An amount of the peroxide is from 0.45 to 0.5 mol based on 1 mol of phenyl sulfide, and the time of adding the peroxide is controlled at 2 to 10 hours.

In step 1), the halogenating agent can be, for example, a variety of commonly used halides, etc. from the perspective of yield. Furthermore, the halogenating agent can be a halide of metal, preferably a halide of alkali metal. The halide of the present disclosure is preferably one or more sodium bromide and potassium bromide, more preferably sodium bromide; the inorganic acid is one or more sulfuric acids, hydrochloric acids, and phosphoric acids, preferably sulfuric acids; based on 1 mol of phenyl sulfide, an amount of the halogenating agent is from 0.9 to 1.0 mol, preferably from 0.95 to 0.99 mol; an amount of the inorganic acid is from 0.9 to 1.0 mol, preferably from 0.95 to 0.99 mol. By limiting the amounts of the halogenating agent and the inorganic acid within the above ranges, the content of halide and the amount of waste acids in the reaction system can be reduced so as to minimize impacts on the environment.

In step 1), the halogenation reaction adopts a two-phase system and it takes place in an organic phase. Therefore, the organic solvent can be selected from non-polar solvents commonly used in the art, for instance, non-polar halogenated hydrocarbon-based solvents, etc., and is preferably one or more dichloromethane, chloroform, carbon tetrachloride, and dichloroethane, more preferably dichloromethane; based on 1 mol of phenyl sulfide, an amount of the organic solvent is from 4 to 6 mol.

In step 1), the temperature for the halogenation reaction is from 10° C. to 40° C., and a total reaction time is from 4 to 15 hours.

The halogenation reaction according to the present disclosure occurs at the 4-position of the benzene in the phenyl sulfide. In addition, by modulating an amount ratio of the above phenyl sulfide to the halogenating agent, the halogenation reaction is controlled to occur mainly on one benzene ring in the phenyl sulfide.

Typically, when sodium bromine and sulfuric acid are used, the equation for the halogenation reaction in the present embodiment is as follows:

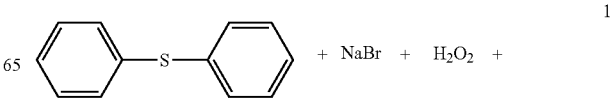

1

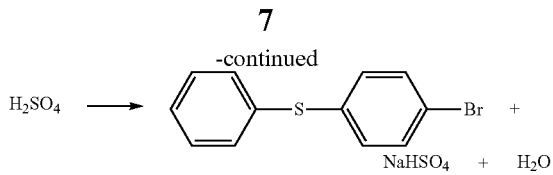

After the completion of the halogenation reaction, the system is left to stand for delamination and the system is divided into an aqueous layer and an organic layer, which are separated by conventional equipment, such as a liquid separator. The resulting aqueous layer contains an acidic material, for instance, in a preferred embodiment of the present disclosure, the acidic material can be a hydrogen sulfate of metal, e.g., NaHSO$_4$. Such aqueous layer containing an acidic material and an organic layer are usable, for example, the aqueous layer can be used directly as an acidic solution in the acidification step as described below, and after separation of the product and recycling of the solvents, the organic layer can be used for extraction of the organic phase in the process of separation of the product resulting from the sulfhydrylation reaction described below. Recycling of the aqueous layer and the organic layer can guarantee full use of various components resulting from the preparation method according to the present disclosure to reduce production of wastes and the costs.

Sulfhydrylation Reaction

In the present embodiment, the 4-halophenyl sulfide prepared in step 1) and a SMAB-NaHS complex are subjected to a sulfhydrylation reaction to obtain 4-phenylthio-phenyl-thiolate.

The sulfhydrylation reaction according to the present disclosure is a reaction performed in the presence of a thiolation reagent that can be hydrosulfide of metal. In a preferred embodiment of the present disclosure, the sulfhydrylation reaction is carried out in the presence of a SMAB-NaHS complex; the SMAB is a sodium 4-methylamino-butyrate, and the NaHS is sodium hydrosulfide.

In the above-mentioned preferred embodiment of the present disclosure, the SMAB-NaHS complex enables an increase in nucleophilic activity of S, which facilitates its sulfhydrylation reaction with the 4-halophenyl sulfide, thereby increasing a yield of the product.

In the present embodiment, the sulfhydrylation reaction equation is as follows:

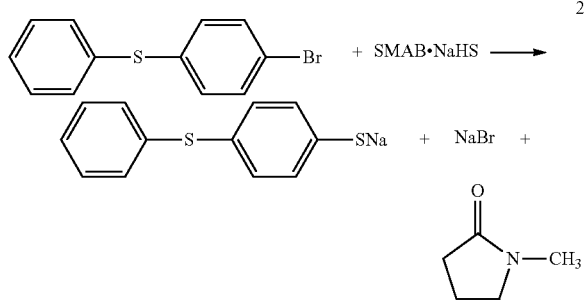

In step 2), based on 1 mol of phenyl sulfide, an amount of the SMAB-NaHS complex is from 0.9 to 1.0 mol, preferably from 0.95 to 0.99 mol.

In step 2), the sulfhydrylation reaction is carried out at 150 to 230° C., preferably 180 to 210° C., and the time of the sulfhydrylation reaction is 3 to 6 hours.

The sulfhydrylation reaction can be carried out in the presence of an organic solvent. The organic solvent can be selected from polar solvents, preferably NMP. The NMP may be unused NMP, but it is preferably selected from the NMPs introduced when SMAB-NaHS is prepared below. After the sulfhydrylation reaction ends, the reactant is subjected to a desolvation treatment and NMP therein is recycled for use as a solvent for preparing SMAB-NaHS. Thereafter, the desolventized system is separated by extraction to gain an organic phase and an aqueous phase.

The extracting agent can be an organic solvent and optionally an aqueous phase, and the organic solvent can be the organic solvent recycled from the halogenation reaction as described above. After separation, an aqueous layer containing phenylthio-benzenethiolate is obtained.

In the sulfhydrylation reaction, in a preferred embodiment of the present disclosure, the SMAB-NaHS complex is used as a preferred thilation reagent and it may be a commercially available product or obtainable according to a general method in the art. Preferably, the SMAB-NaHS complex according to the present disclosure can be prepared by the following method:

a. adding an aqueous solution of sodium hydroxide to a NMP solvent, and dehydrating the reactant upon completion of the reaction;

b. upon completion of the dehydration, adding an aqueous solution of sodium hydrosulfide and then subjecting to dehydration to obtain a SMAB-NaHS complex.

The reaction equation of the SMAB-NaHS complex is shown below:

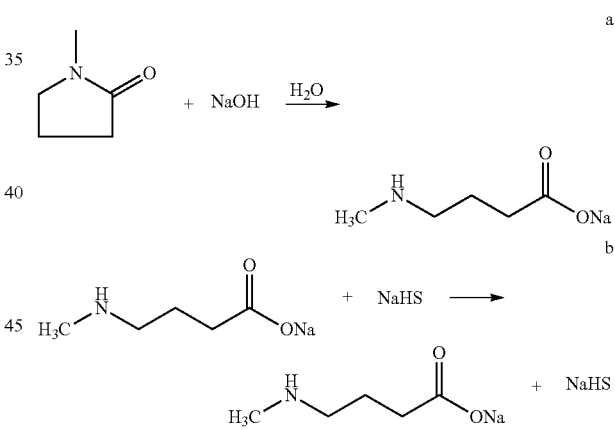

In step a, NMP and an alkaline substance form sodium 4-methylamino-butyrate (SMAB) in the presence of water. In this step, an amount of the sodium hydroxide is from 0.9 to 1.0 mol based on 1 mol of phenyl sulfide.

In step b, the metal hydrosulfide is selected from hydrosulfides of alkali metals, further preferably sodium hydrosulfides. Based on 1 mol of phenyl sulfide, an amount of the NMP is from 4.0 to 5.0 mol, and an amount of the metal hydrosulfide (NaHS) is from 0.9 to 1.0 mol.

In step b, under the dehydration condition, SMAB and NaHS are mixed and heated to give a complex, i.e., a SMAB-NaHS complex. The dehydration process is conducted at 180° C. to 250° C. After dehydration, an organic solvent, preferably NMP, can be supplemented at a desired amount as needed.

In a conventional one-step dehydration process, NaHS and NMP are added to be dehydrated together with NaOH, but as the dehydration step lasts for a very long time period, a relatively more content of sulfur (hydrogen sulfide) is lost by volatilization. The present disclosure improves the conventional dehydration method, and adopts a two-step dehydration method, in which source of sulfur is not added in the first step and thus the loss of source of sulfur is reduced.

After the sulfhydrylation reaction is finished, 4-phenylthio-phenylthiolate is produced in the reaction system, and to ease the subsequent acidification step, an extraction technique is utilized to separate 4-phenylthio-phenylthiolate from the reaction system. The organic solvent used for extraction can be identical or not identical with the kind of the organic solvent used in step 1), preferably, both of them are identical for sake of recycling. As noted above, the solvent used for extraction herein is preferably the solvent recycled from the organic layer after the reaction of step 1) ends, and a part of water from the perspective of cost saving and environment friendliness.

Acidification Reaction

In the present embodiment, 4-phenylthio-benzenethiol is obtained by acidifying 4-phenylthio-phenylthiolate. In the present embodiment, the mode or condition of carrying out acidification reaction is not in particular limited. Preferably, the acidification reaction is performed in a weak acidic aqueous solution, such as a $NaHSO_4$ or $KHSO_4$ aqueous solution, which can decrease corrosion damage to reaction equipment, prolong its service life and save production costs. As disclosed above, the acidification reaction can make use of the aqueous layer derived from separation after completion of the reaction in step 1), so that the acidic aqueous layer resulting from step 1) can be fully utilized.

Typically, in the present embodiment, when a $NaHSO_4$ aqueous solution is used, the equation of the acidification reaction is as follows:

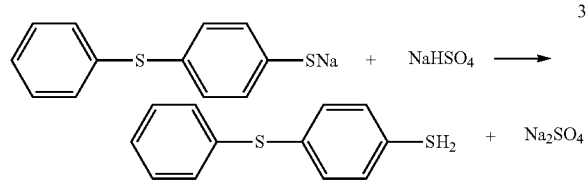

While obtaining a major product 4-phenylthio-benzenethiol, the present disclosure is also capable of gaining a hydrated $Na_2SO_4$ product with a very high purity, and because of a very high purity of such a product and relatively simple reactants participating in the reaction of producing the product and reaction process, the hydrated $Na_2SO_4$ product is obtainable from direct separation or mere simple processing, such as recrystallization. Therefore, the economical efficiency of the method according to the present disclosure is further increased.

Besides, the equipment used in the present embodiment is not limited in principle as long as it can realize the above reactions or processes.

The Second Embodiment

The second embodiment of the present disclosure provides a preparation method for 4-phenylthio-benzenethiol. The raw materials, solvents, water and the like used during the preparation are recycled. That is to say, in the present embodiment, except that raw materials essential for the initial reaction are all unused new materials, the aqueous phase and organic solvents produced in steps 1) to 3) of the present disclosure are recycled during the subsequent consecutive production. A total recycling rate of the aqueous phase and the organic phase is 80%, preferably 90% or more, more preferably 95% or more, most preferably approximate 100%.

In the present embodiment, the halogenation reaction in step 1) adopts a two-phase system. The halogenation reaction occurs in the organic phase, and the inorganic salt produced in the reaction process is left in the aqueous phase.

In consideration of recycling of the aqueous layer in step 1), the inorganic acid in step 1) is preferably a strong inorganic acid, more preferably a sulfuric acid. After the halogenation reaction is finished, delamination is performed to give an aqueous layer containing a strong acid salt, which is acidic and is directly usable for the acidification reaction in the subsequent step 3) through the pipeline of the equipment, that is, the acidification reaction in the step 3): the aqueous layer obtained by delamination in step 1) is added to the aqueous layer obtained by delamination and separation in step 2) for an acidification reaction, and after the reaction is completed, delamination is carried out and the organic layer is 4-phenylthio-benzenethiol.

Typically, sodium bromide as a halogenating agent and sulfuric acid are taken as an example. Delamination is performed following the halogenation reaction to give an aqueous layer containing $NaHSO_4$, which can be directly used for the acidification reaction in the subsequent step 3); moreover, in the case of subjecting to the acidification reaction, $NaHSO_4$ turns into $Na_2SO_4$; delamination is performed following the acidification reaction, and a $Na_2SO_4$ product containing crystal water is obtained through simple cooling crystallization subsequently. The precipitated $Na_2SO_4$ product containing crystal water generally exists in the form of $Na_2SO_4 \cdot 10H_2O$. After the aqueous layer resulting from delamination following the acidification reaction precipitates $Na_2SO_4$ containing crystal water by cooling crystallization, the remaining mother solution is properly concentrated and then directly recycled as a raw material (containing a halogenating agent and a few 4-phenylthio-phenylthiolate) for the halogenation reaction in step 1), and the recycled water may be used for the extraction of the sulfhydrylation reaction in step 2).

After the halogenation reaction is finished, the reaction system is delaminated to give an organic layer, from which the recycled organic solvent is removed; the organic solvent charged with water as required may be used as an extracting agent for the extraction in step 2).

As can be appreciated from the explanation on step 2), the NMP is not only a raw material for synthesizing a SMAB-NaHS complex but also a solvent for the sulfhydrylation reaction. After the sulfhydrylation reaction is terminated, the NMP is removed and the recycled NMP by removal can be directly used to prepare a SMAB-NaHS complex.

After the step of removing NMP described above, the extraction operation in step 2) is performed followed by delamination to obtain an organic layer containing a small amount of unbrominated phenyl sulfide and a small amount of non-thiolated 4-halophenyl sulfide, and an aqueous layer containing 4-phenylthio-phenylthiolate. The organic layer can be recycled back to step 1) and used as an organic solvent for the bromination reaction in step 1), wherein a small amount of unbrominated phenyl sulfide and a small amount of non-thiolated 4-halophenyl sulfide included therein are directly used as raw materials to participate in the reaction.

EXAMPLES

Here are examples provided for further describing the present disclosure, but the present disclosure is not limited to these examples.

Example 1

1) Halogenation Reaction 34.0 kg (400 mol) of dichloromethane, 18.6 kg (100 mol) of phenyl sulfide, 9.27 kg (90 mol) of sodium bromide, and 44.1 kg (90 mol) of 20% sulfuric acid were charged to a glass-lined reactor, and while stirred, the mixture was heated at 40° C. under nitrogen protection. Thereafter, 5.1 kg (45 mol) of 30% hydrogen peroxide was added dropwise to the reactor, and the dropping time was controlled at 2 hours. After the dropping was finished, the reaction continued for 2 hours on the condition of heat preservation. Upon completion of the reaction, the resulting reaction mixture was left to stand and delaminated; the aqueous layer was used for the acidification reaction in step 3), while the organic layer was desolventized to give 4-bromophenylsulfide, and 33.1 kg of the desolventized dichloromethane was used in the extraction process of step 2).

2) Sulfhydrylation Reaction 39.6 kg (400 mol) of N-methyl-2-pyrrolidone (hereinafter referred to as NMP) and 7.2 kg (90 mol) of 50% aqueous sodium hydroxide solution were charged to a stainless steel reactor, and heated at 100° C. with stirring under nitrogen protection, followed by heat preservation for 2 hours. After the heat preservation, the mixture was heated at 190° C. at a velocity of 1.5° C./min, and 3.96 kg of aqueous solution (containing 91% water) was dehydrated before lowering the temperature to 110° C. again. 10.1 kg (90 mol) of 50% sodium sulfide was added, and then the mixture was further heated at 180° C. at a velocity of 1.5° C./min, with 5.5 kg of aqueous solution (containing 92% water) dehydrated. After dehydration, 0.8 kg of NMP was supplemented, and the temperature was lowered to 150° C., thereby obtaining a SMAB-NaHS complex.

The 4-bromophenylsulfide obtained in step 1) and the SMAB-NaHS complex were mixed, and heated at 250° C. with stirring under nitrogen protection for a sulfhydrylation reaction, and the reaction was held for 3 hours. After the reaction was completed, the reaction mixture was cooled at 180° C. for reduced pressure distillation to desolventize 39.5 kg of NMP, which could be directly applied to the next preparation process of an SMAB-NaHS complex. After desolvation, 33.1 kg of dichloromethane obtained by the desolvation in step 1) and 50 kg of water were added for extraction and delamination, and an organic layer (dichloromethane solution containing 10.5 mol phenyl sulfide and 1.2 mol 4-bromophenylsulfide) was recycled and used for the next bromination reaction in step 1). The aqueous layer obtained by delamination was an aqueous solution containing sodium bromide and sodium 4-phenylthio-phenylthiolate.

3) Acidification Reaction

The aqueous layer obtained by delamination in step 1) was added to the aqueous solution containing sodium bromide and sodium 4-phenylthio-phenylthiolate obtained in step 2), and stirred for 30 min. After the reaction is finished, the mixture was left to stand and delaminated. The organic layer was dehydrated under reduced pressure to obtain 16.4 kg (88.3 mol) of 4-phenylthio-benzenethiol.

An aqueous phase obtained by delamination was cooled down to 2° C. by stages to precipitate 29.1 kg of $Na_2SO_4 \cdot 10H_2O$. After concentration, the mother solution could be used in step 1) as a brominating agent, and the recycled water could be used for extraction in step 2).

Example 2

1) Halogenation Reaction

To a glass-lined reactor were charged the organic layer (dichloromethane solution containing 10.5 mol phenyl sulfide and 1.2 mol 4-bromophenylsulfide) recycled from the sulfhydrylation reaction in Example 1, 16.42 kg (88.3 mol) of phenyl sulfide, the mother solution obtained in step 3) of Example 1, and 9.0 kg (90 mol) of 98% sulfuric acid. While stirred, the mixture was heated at 40° C. under nitrogen protection. Thereafter, 5.1 kg (45 mol) of 30% hydrogen peroxide was added dropwise to the reactor, and the dropping time was controlled at 2 hours. After the dropping was finished, the reaction continued for 2 hours on the condition of heat preservation. Upon completion of the reaction, the resulting reaction mixture was left to stand and delaminated; the aqueous layer was used for the acidification reaction in step 3), while the organic layer was desolventized to obtain 4-bromophenylsulfide, and 33.0 kg of the desolventized dichloromethane was used in the extraction process of step 2).

2) Sulfhydrylation Reaction

To a stainless steel reactor were charged 39.5 kg of NMP obtained by desolvation in the process of sulfhydrylation reaction in Example 1, with 0.1 kg of NMP supplemented (400 mol in total), and 7.2 kg (90 mol) of 50% aqueous sodium hydroxide solution. The mixture was heated at 100° C. with stirring under nitrogen protection, followed by heat preservation for 2 hours. After the heat preservation, the mixture was heated at 190° C. at a velocity of 1.5° C./min, and 3.96 kg of aqueous solution (containing 91% water) was dehydrated before lowering the temperature to 110° C. 10.1 kg (90 mol) of 50% sodium sulfide was added, and then the mixture was further heated at 180° C. at a velocity of 1.5° C./min, with 5.5 kg of aqueous solution (containing 92% water) dehydrated. After dehydration, 0.8 kg of NMP was supplemented, and the temperature was lowered to 150° C., thereby obtaining a SMAB-NaHS complex.

The 4-bromophenylsulfide obtained in step 1) and the SMAB-NaHS complex were mixed, and heated at 250° C. with stirring under nitrogen protection for a sulfhydrylation reaction, and the reaction was held for 3 hours. After the reaction was completed, the reaction mixture was cooled at 180° C. for reduced pressure distillation to desolventize 39.5 kg of NMP, which could be directly applied to the next preparation process of an SMAB-NaHS complex. After desolvation, 33.0 kg of dichloromethane obtained by the desolvation in step 1) and 50 kg of water were added for extraction and delamination, and an organic layer (dichloromethane solution containing 10.3 mol phenyl sulfide and 1.4 mol 4-bromophenylsulfide) was recycled and used for the next bromination reaction in step 1). The aqueous layer obtained by delamination was an aqueous solution containing sodium bromide and sodium 4-phenylthio-phenylthiolate.

3) Acidification Reaction

The aqueous layer obtained by delamination in step 1) was added to the aqueous solution containing sodium bromide and sodium 4-phenylthio-phenylthiolate obtained in step 2), and stirred for 30 min. After the reaction was completed, the mixture was left to stand and delaminated. The organic layer was dehydrated under reduced pressure to obtain 16.4 kg (88.3 mol) of 4-phenylthio-benzenethiol. The yield was 100% as per newly charged phenyl sulfide.

An aqueous phase obtained by delamination was cooled down to 2° C. by stages to precipitate 30.5 kg of $Na_2SO_4 \cdot 10H_2O$. After concentration, the mother solution could be used in step 1) as a brominating agent, and the recycled water could be used for extraction in step 2).

Example 3

1) Halogenation Reaction

To a glass-lined reactor were charged the organic layer (dichloromethane solution containing 10.3 mol phenyl sulfide and 1.4 mol 4-bromophenylsulfide) recycled from the sulfhydrylation reaction in Example 2, 8.5 kg (100 mol) of dichloromethane, 16.42 kg (88.3 mol) of phenyl sulfide, the mother solution obtained in step 3) of Example 1, 0.52 kg (5 mol) of sodium bromide, and 9.5 kg (95 mol) of 98% sulfuric acid. The temperature of the mixture was changed to 20° C. with stirring under nitrogen protection. Thereafter, 5.38 kg (47.5 mol) of 30% hydrogen peroxide was added dropwise to the reactor, and the dropping time was controlled to be 6 hours. After the dropping was finished, the reaction continued for 3 hours on the condition of heat preservation.

Upon completion of the reaction, the resulting reaction mixture was left to stand and delaminated; the aqueous layer was used for the acidification reaction in step 3), while the organic layer was desolventized to obtain 4-bromophenylsulfide, and 41.2 kg of the desolventized dichloromethane was used in the extraction process of step 2).

2) Sulfhydrylation Reaction

To a stainless steel reactor were charged 39.5 kg of NMP obtained by desolvation in the process of sulfhydrylation reaction in Example 2, with 5.05 kg of NMP supplemented (450 mol in total), and 7.6 kg (95 mol) of 50% aqueous sodium hydroxide solution. The mixture was heated at 100° C. with stirring under nitrogen protection, followed by heat preservation for 2 hours. After the heat preservation, the mixture was heated at 190° C. at a velocity of 1.5° C./min, and 4.18 kg of aqueous solution (containing 91% water) was dehydrated before lowering the temperature to 110° C. 10.64 kg (95 mol) of 50% sodium sulfide was added, and then the mixture was further heated at 210° C. at a velocity of 1.5° C./min, with 6.1 kg of aqueous solution (containing 87.2% water) dehydrated. After dehydration, 1.16 kg of NMP was supplemented, and the temperature was lowered to 150° C., thereby obtaining a SMAB-NaHS complex.

The 4-bromophenylsulfide obtained in step 1) and the SMAB-NaHS complex were mixed, and heated at 210° C. under nitrogen protection for a sulfhydrylation reaction, and the reaction was held for 4 hours. After the reaction was completed, the reaction mixture was cooled at 180° C. for reduced pressure distillation to desolventize 44.3 kg of NMP, which could be directly applied to the next preparation process of an SMAB-NaHS complex. After desolvation, 41.2 kg of dichloromethane obtained during the desolvation in step 1) and 55 kg of water were added for extraction and delamination, and an organic layer (dichloromethane solution containing 5.5 mol phenyl sulfide and 1.3 mol 4-bromophenylsulfide) was recycled and used for the next bromination reaction in step 1). The aqueous layer obtained by delamination was an aqueous solution containing sodium bromide and sodium 4-phenylthio-phenylthiolate.

3) Acidification Reaction

The aqueous layer obtained by delamination in step 1) was added to the aqueous solution containing sodium bromide and sodium 4-phenylthio-phenylthiolate obtained in step 2), and stirred for 30 min. After the reaction, the mixture was left to stand and delaminated. The organic layer was dehydrated under reduced pressure to obtain 20.32 kg (93.2 mol) of 4-phenylthio-benzenethiol.

An aqueous phase obtained by delamination was cooled down to 2° C. by stages to precipitate 32.2 kg of $Na_2SO_4 \cdot 10H_2O$. After concentration, the mother solution could be used in step 1) as a brominating agent, and the recycled water could be used for extraction in step 2).

Example 4

1) Halogenation Reaction

To a glass-lined reactor were charged the organic layer (dichloromethane solution containing 5.5 mol phenyl sulfide and 1.3 mol 4-bromophenylsulfide) recycled from the sulfhydrylation reaction in Example 3, 8.5 kg (100 mol) of dichloromethane, 17.34 kg (93.2 mol) of phenyl sulfide, the mother solution obtained in step 3) of Example 2, 0.52 kg (5 mol) of sodium bromide, and 10.0 kg (100 mol) of 98% sulfuric acid. The temperature of the mixture was changed to 10° C. with stirring under nitrogen protection. Thereafter, 5.67 kg (50 mol) of 30% hydrogen peroxide was added dropwise to the reactor, and the dropping time was controlled at 10 hours. After the dropping was finished, the reaction continued for 5 hours on the condition of heat preservation. Upon completion of the reaction, the resulting reaction mixture was left to stand and delaminated; the aqueous layer was used for the acidification reaction in step 3), while the organic layer was desolventized to obtain 4-bromophenylsulfide, and 49.5 kg of the desolventized dichloromethane was used in the extraction process of step 2).

2) Sulfhydrylation Reaction

To a stainless steel reactor were charged 44.3 kg of NMP obtained by desolvation in the process of sulfhydrylation reaction in Example 3, with 5.2 kg of NMP supplemented (500 mol in total), and 8.0 kg (100 mol) of 50% aqueous sodium hydroxide solution. The mixture was heated at 100° C. with stirring under nitrogen protection, followed by heat preservation for 2 hours. After the heat preservation, the mixture was heated at 190° C. at a velocity of 1.5° C./min, and 4.4 kg of aqueous solution (containing 91% water) was dehydrated before lowering the temperature to 110° C. 11.2 kg (100 mol) of 50% sodium sulfide was added, and then the mixture was further heated at 250° C. at a velocity of 1.5° C./min, with 6.5 kg of aqueous solution (containing 86.2% water) dehydrated. After dehydration, 1.3 kg of NMP was supplemented, and the temperature was lowered to 150° C., thereby obtaining a SMAB-NaHS complex.

The 4-bromophenylsulfide obtained in step 1) and the SMAB-NaHS complex were mixed, heated at 150° C. for 3 hours under nitrogen protection, and then heated at 230° C. following heat preservation for 2 hours for a sulfhydrylation reaction. After the reaction was completed, the reaction mixture was cooled at 180° C. for reduced pressure distillation to desolventize 49.3 kg of NMP, which could be directly applied to the next preparation process of an SMAB-NaHS complex. After desolvation, 49.5 kg of dichloromethane obtained during the desolvation in step 1) and 60 kg of water were added for extraction and delamination, and an organic layer (dichloromethane solution containing 0.6 mol phenyl sulfide and 1.1 mol 4-bromophenylsulfide) was recycled and used for the next bromination reaction in step 1). The aqueous layer obtained by delamination was an aqueous solution containing sodium bromide and sodium 4-phenylthio-phenylthiolate.

3) Acidification Reaction

The aqueous layer obtained by delamination in step 1) was added to the aqueous solution containing sodium bromide and sodium 4-phenylthio-phenylthiolate obtained in step 2), and stirred for 30 min. After the reaction, the mixture was left to stand and delaminated. The organic layer was dehydrated under reduced pressure to obtain 21.52 kg (98.7 mol) of 4-phenylthio-benzenethiol.

An aqueous phase obtained by delamination was cooled down to 2° C. by stages to precipitate 33.7 kg of $Na_2SO_4 \cdot 10H_2O$. After concentration, the mother solution could be used in step 1) as a brominating agent, and the recycled water could be used for extraction in step 2).

Practicability

The method for preparing 4-phenylthio-benzenethiol as provided by the present disclosure is relatively simple and very convenient to recycle raw materials and solvents, realizes the reuse of raw materials, solvents, etc., and is applicable to industrial mass production.

What is claimed is:

1. A preparation method for 4-phenylthio-benzenethiol, comprising the steps of:
   subjecting phenyl sulfide as a raw material to a halogenation reaction to obtain 4-halophenyl sulfide;
   subjecting the 4-halophenyl sulfide to a sulfhydrylation reaction to obtain 4-phenylthio-phenylthiolate; and
   subjecting the 4-phenylthio-phenylthiolate to acidification;
   wherein
   the halogenation reaction is: adding peroxide to a mixed solution containing phenyl sulfide, an organic solvent, a halogenating agent, and an inorganic acid to undergo a halogenation reaction, and obtaining 4-halophenyl sulfide by separation;
   the sulfhydrylation reaction is: subjecting the resulting 4-halophenyl sulfide and a SMAB-NaHS complex to a sulfhydrylation reaction, and obtaining an aqueous layer containing 4-phenylthio-phenylthiolate by extraction and separation; and
   the acidification reaction is: subjecting the aqueous layer containing 4-phenylthio-phenylthiolate to an acidification reaction in an acidic aqueous solution, and obtaining the 4-phenylthio-benzenethiol by separation.

2. The preparation method according to claim 1, wherein, in the halogenation reaction,
   the halogenating agent is one or more selected from the group consisting of sodium bromide and potassium bromide;
   the inorganic acid is one or more selected from the group consisting of sulfuric acid, hydrochloric acid, and phosphoric acid;
   based on 1 mol of phenyl sulfide, an amount of the halogenating agent is from 0.9 to 1.0 mol; and an amount of the inorganic acid is from 0.9 to 1.0 mol.

3. The preparation method according to claim 1, wherein, in the halogenation reaction,
   the organic solvent is one or more selected from the group consisting of dichloromethane, chloroform, carbon tetrachloride, and dichloroethane;
   based on 1 mol of phenyl sulfide, an amount of the organic solvent is from 4 to 6 mol.

4. The preparation method according to claim 1, wherein, in the halogenation reaction,
   the peroxide is hydrogen peroxide;
   an amount of the peroxide is from 0.45 to 0.5 mol based on 1 mol of phenyl sulfide; and
   the time of adding the peroxide is controlled at 2 to 10 hours, and the peroxide is added dropwise.

5. The preparation method according to claim 1, wherein, in the halogenation reaction, the temperature for the halogenation reaction is from 10° C. to 40° C., and a total reaction time is from 4 to 15 hours.

6. The preparation method according to claim 1, wherein, in the sulfhydrylation reaction, based on 1 mol of phenyl sulfide, an amount of the SMAB-NaHS complex is from 0.9 to 1.0 mol.

7. The preparation method according to claim 1, wherein, in the sulfhydrylation reaction, the SMAB-NaHS complex is prepared by the following method:
   a. adding a sodium hydroxide aqueous solution to an NMP solvent, and after the reaction is completed, subjecting the reactant to dehydration; and
   b. adding a sodium hydrosulfide aqueous solution prior to dehydration to obtain a SMAB- NaHS complex.

8. The preparation method according to claim 7, wherein, based on 1 mol of phenyl sulfide, an amount of the sodium hydroxide is from 0.9 to 1.0 mol; an amount of the NMP solvent is from 4.0 to 5.0 mol; and an amount of the sodium hydrosulfide is from 0.9 to 1.0 mol.

9. The preparation method according to claim 7, wherein the dehydration in steps a and b is carried out at 180° C. to 250° C.

10. The preparation method according to claim 1, wherein,
    the sulfhydrylation reaction is carried out at 150° C. to 230° C.; and the time of the sulfhydrylation reaction is 3 to 6 hours.

11. The preparation method according to claim 1, wherein,
    after the sulfhydrylation reaction is completed, desolvation is performed prior to extraction and separation; and
    NMP recycled by desolvation is capble of being directly used for the preparation of a SMAB-NaHS complex.

12. The preparation method according to claim 1, wherein,
    after the halogenation reaction is completed, an aqueous layer and an organic layer are obtained by separation; where
    the aqueous layer is used as an acidic aqueous solution in the acidification reaction; and
    the organic layer is desolventized and recycled to obtain a solvent, to which water is added, for use in extraction carried out following the sulfhydrylation reaction.

13. The preparation method according to claim 12, wherein an organic layer obtained by extraction and separation after the sulfhydrylation reaction is used as a solvent in the halogenation reaction.

14. The preparation method according to claim 1, wherein,
    delamination is performed following the acidification reaction;
    the resulting aqueous layer is subjected to cooling crystallization to give $Na_2SO_4$ containing crystal water; and
    the remaining mother solution is concentrated and then used as a raw material for the halogenation reaction.

15. The preparation method according to claim 1, wherein,
    based on 1 mol of phenyl sulfide, an amount of the halogenating agent is from 0.95 to 0.99 mol; and an amount of the inorganic acid is from 0.95 to 0.99 mol.

16. The preparation method according to claim 6, wherein,
   in the sulfhydrylation reaction, based on 1 mol of phenyl sulfide, an amount of the SMAB-NaHS complex is from 0.95 to 0.99 mol.

17. The preparation method according to claim 1, wherein, the sulfhydrylation reaction is carried out at 150° C. to 230° C.; and the time of the sulfhydrylation reaction is 3 to 6 hours.

18. The preparation method according to claim 1, wherein, the sulfhydrylation reaction is carried out at 180° C. to 210° C.

19. The preparation method according to claim 1, wherein, the sulfhydrylation reaction is carried out at 180° C. to 210° C.

* * * * *